United States Patent [19]
Dørwald

[11] Patent Number: 6,136,984
[45] Date of Patent: *Oct. 24, 2000

[54] SOLID PHASE AND COMBINATORIAL SYNTHESIS OF SUBSTITUTED THIOPHENES AND OF ARRAYS OF SUBSTITUTED THIOPHENES

[75] Inventor: Florencio Zaragoza Dørwald, Herlev, Denmark

[73] Assignee: Novo Nordisk A/S, Bagsvaerd, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/842,737

[22] Filed: Apr. 16, 1997

[30] Foreign Application Priority Data

Apr. 22, 1996 [DK] Denmark .................................. 475/96

[51] Int. Cl.⁷ ..................... C07D 331/02; C07D 333/02; C07D 333/36; A01N 43/02
[52] U.S. Cl. .................................. 549/1; 549/29; 549/68; 549/70; 514/430; 514/438
[58] Field of Search ................................... 549/68, 70, 1, 549/29; 544/374; 514/447, 253, 430, 438; 436/518, 523–531

[56] References Cited

U.S. PATENT DOCUMENTS

| | | | |
|---|---|---|---|
| 3,284,453 | 11/1966 | Tomcufak et al. | 544/374 |
| 3,445,473 | 5/1969 | Ruschig et al. | 549/68 |
| 3,506,669 | 4/1970 | Laliberte | 549/68 |
| 3,639,613 | 2/1972 | Dunn et al. | 549/68 |
| 3,823,161 | 7/1974 | Lesser | 549/68 |
| 3,833,677 | 9/1974 | Grard | 549/70 |
| 3,963,750 | 6/1976 | Goudie | 549/68 |
| 4,108,867 | 8/1978 | Bard et al. | 549/68 |
| 4,240,820 | 12/1980 | Dickone et al. | 549/68 |
| 4,472,425 | 9/1984 | Sandmeier et al. | 549/68 |
| 4,767,758 | 8/1988 | Breccia et al. | 514/447 |
| 5,201,934 | 4/1993 | Muenster et al. | 504/289 |
| 5,679,800 | 10/1997 | Egli et al. | 549/68 |
| 5,698,581 | 12/1997 | Kleemann et al. | 514/447 |

FOREIGN PATENT DOCUMENTS 0154363 3/1982 Germany .

OTHER PUBLICATIONS

E. M. Gordon et al. J. Med. Chem., vol. 37, pp. 1385–1401, May 1994.
Eduard R. Felder, Chimia, vol. 48, pp. 531–541, (1994).
Eric M. Gordon, Current Biology Ltd., vol. 6, pp. 624–631, (1995).
Fruchtel, et al., Angew Chem. Int., vol. 35, pp. 17–42 (1996).

Primary Examiner—Bennett Celsa
Assistant Examiner—P. Ponnaluri
Attorney, Agent, or Firm—Steve T. Zelson; Carol E. Rozck

[57] ABSTRACT

A solid phase method for the synthesis of a plurality of differently substituted thiophenes with a wide variety of side-chain substituents as compounds of potential therapeutic interest is disclosed. The thiophenes are prepared by acylation of a substrate-bound primary or secondary amine with cyanoacetic acid and reaction of the resulting cyanoacetamide with an isothiocyanate in the presence of a base. Alkylation with an appropriate alkyl halide, followed by Thorpe-Ziegler-cyclization yields differently substituted, support-bound 3-aminothiophenes. These may be screened on the substrate or cleaved from the substrate and then screened in solution. Alternatively, the resin-bound 3-amino thiophenes or the synthetic intermediates can be subjected to further synthetic transformations (N-acylation, reduction) on the support, which permits the preparation of further therapeutically interesting compounds. The efficient synthesis of a wide variety of thiophenes using automated synthesis technology of the present method makes these compounds attractive candidates for the generation and rapid screening of diverse thiophene-based libraries. The method disclosed here provides an easy and fast access to highly diverse heterocyclic compounds of therapeutic interest, amenable to automatization.

6 Claims, No Drawings

SOLID PHASE AND COMBINATORIAL SYNTHESIS OF SUBSTITUTED THIOPHENES AND OF ARRAYS OF SUBSTITUTED THIOPHENES

CROSS-REFERENCE TO RELATED APPLICATIONS

This application claims priority under 35 U.S.C. 119 of Danish application 475/96 filed Apr. 22, 1996, the contents of which are fully incorporated herein by reference.

BACKGROUND OF THE INVENTION

The present invention relates to the field of solid phase chemistry. More specifically, the invention provides a method for solid phase and combinatorial synthesis of organic compounds, and most particularly, a therapeutically important class of compounds, namely diversely substituted 3-aminothiophenes.

Obtaining a better understanding of the important factors in molecular recognition in conjunction with developing new therapeutic agents is a major focus of scientific research. Methods have recently been developed, which permit the fast generation of large arrays of pure compounds or of mixtures of compounds, which are then screened against a specific receptor or enzyme. However, there are still only few methods available for the fast synthesis of organic compounds other than peptides or oligonucleotides. The latter tend to have very short clearing times, so that their utility as bioavailable therapeutic agent will be limited. For this reason, organic compounds of potential therapeutic interest are today still synthesized and evaluated one at a time, thus dramatically limiting the number of derivatives which can be screened. It is therefore of utmost importance to develop new synthetic methodology, which permits the fast synthesis of bioavailable organic compounds of potential therapeutic interest, such as small heterocyclic compounds. This could be achieved by developing a solid phase synthesis for such compounds, since experience has shown, that solid phase synthesis is amenable to automatization and can yield products of high purity without the need of any tedious and time consuming purification steps.

The realization of known synthetic reactions on a solid support may not always be possible and may require careful optimization of the reaction conditions. Although solid phase synthesis, once implemented and optimized, offers many advantages if compared to syntheses in liquid phase, the finding of the appropriate reaction conditions may be a difficult task. This may be due to the limited choice of solvents which may be used with some types of supports, as well as the difficulty of precise temperature adjustment in arrays of reactors for solid phase synthesis. Additionally, the classical tools for the quality control of intermediates (infrared spectroscopy, nuclear magnetic resonance spectroscopy, mass spectrometry) may only be of limited use in solid phase synthesis. For these reasons, the implementation of known reactions to a solid support may often require a major effort and time investment.

The synthetic sequence disclosed in this invention is a variant of related thiophene syntheses (ref. 11–16), adapted and optimized for its realization on a solid support.

Terminology

The following terms are intended to have the following, general meanings:

1. Substrate: refers to any insoluble or partially insoluble material, to which compounds may be covalently attached. Substrates may be selected from the group consisting of any kind of organic or inorganic polymeric or oligomeric compound, e.g. polystyrene with different grades of crosslinking, polyethylene glycol (PEG), polyethylene glycol attached to polystyrene (e.g. TentaGel), polyacrylamides, polyacrylates, polyurethanes, polycarbonates, polyamides, polysaccharides or silicates.

2. Linker: a molecule with at least two reactive sites, which permit its covalent attachment to other molecules or to a substrate. Either the bond of the linker to the substrate or the bond of the linker to other molecules attached to it or the linker itself must be cleavable upon selective exposure to an activator such as a selected chemical activator or other specific conditions, e.g. by treatment with a strong acid or by exposure to electromagnetic radiation or by metal catalysis.

3. Array: A collection of N single compounds or N mixtures of compounds with a common structural element, synthesized simultaneously in a parallel fashion using the same synthetic reaction sequence. The precise structure of a single compound within an array of compounds or the components of a mixture within an array of mixtures is determined by the sequence of reactants which gave rise to this compound or mixture and can be deduced from the recorded reaction-protocol. The spatial arrangement of the array is irrelevant.

4. Thiophene: Five-membered heteroaromatic compound containing one sulphur atom in the five-membered ring.

5. Protecting group: A material which is chemically bound to a molecule or a substrate and which may be removed upon selective exposure to an activator such as a selected chemical activator or other specific conditions, e.g. by treatment with a strong acid or by exposure to electromagnetic radiation or by metal catalysis.

6. Combinatorial synthesis: an ordered strategy for parallel synthesis of arrays of single compounds or mixtures, by sequential addition of reagents.

7. Receptor: A material that has an affinity for a given ligand. Receptors may be naturally-occurring or synthetic molecules or aggregates of molecules. Also, they can be employed in their unaltered state or as aggregates with other species. Receptors may be attached, covalently or non-covalently, to a binding material or a substrate, either directly or via a linking substance. Examples of receptors which can be employed by this invention include, but are not restricted to, antibodies, monoclonal antibodies and antisera reactive with specific antigenic determinants (such as viruses, cells or other materials), cell membrane receptors, drugs, oligonucleotides, polynucleotides, nucleic acids, peptides, cofactors, small organic molecules, lectins, sugars, oligosaccharides, cells, cellular membranes, organelles, microorganism receptors, enzymes, catalytic polypeptides, hormone receptors, primary metabolite receptors such as carbohydrate receptors, nucleotide receptors or lipid receptors and secondary metabolite receptors such as opiate receptors, prostaglandine receptors, etc.

8. Abbreviations: The following frequently used abbreviations are intended to have the following meanings:
AcOH: glacial acetic acid
DBU: 1,8-diazabicyclo[5.4.0]undec-7-ene
DCM: dichloromethane, methylenechloride
DMF: N,N-dimethyl formamide
FMoc: fluorenylmethyloxycarbonyl R: organic radical
TFA: trifluoroacetic acid
THF: tetrahydrofurane

SUMMARY OF THE INVENTION

An improved method for the synthesis of therapeutically useful compounds is provided by virtue of the present invention. The invention provides a rapid approach for combinatorial synthesis and screening of arrays of thiophene derivatives as a therapeutically important class of compounds. It provides a solid phase synthesis of these derivatives, which eliminates purification and isolation steps and thus highly increases synthesis efficiency. This patent disclosure also describes an important extension of solid phase synthesis methods to nonoligomeric organic compounds.

A further understanding of the nature and advantages of the invention may be realized by reference to the remaining portions of the specification.

DESCRIPTION

The application of the present invention is the rapid preparation and screening, preferably in parallel and simultaneous fashion, of a large number of differently substituted thiophenes of the general formula I

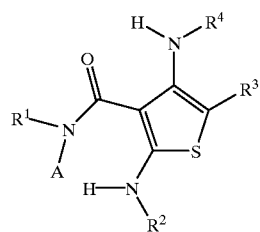

I wherein

A is a hydrogen atom or a group of formula

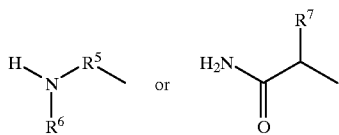

wherein

R$^5$ is alkylene optionally substituted with hydrogen, alkyl, aryl, heteroaryl, alkoxy, aryloxy, cyano, hydroxy, dialkylamino, arylalkylamino, diarylamino or halogen;

R$^6$ is hydrogen, alkyl optionally substituted with hydroxy, halogen, cyano, alkoxy, aryloxy, dialkylamino, arylalkylamino or diarylamino; or aralkyl;

R$^5$ and R$^6$ may be covalently linked to each other by a covalent bond or an additional alkylene group R$^5$, preferentially giving rise to a fragment of the type shown below

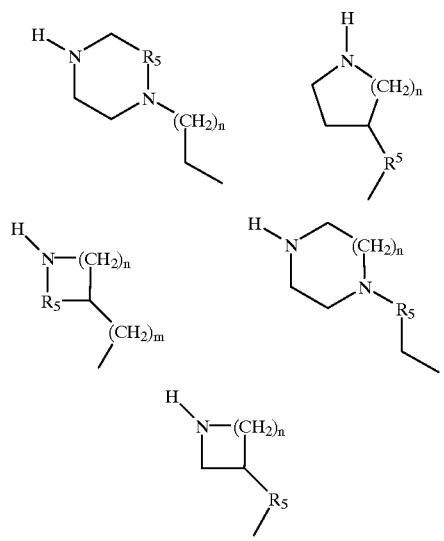

wherein n and m are integers between 0 and 15, preferentially 0 and 3;

R$^7$ is hydrogen, alkyl, alkyl substituted with hydroxy, alkoxy, aryloxy, alkylthio, arylthio, dialkylamino, arylalkylamino or diarylamino; aralkyl, aryl, aryl substituted with alkyl, aryl, heteroaryl, halogen, alkoxy, aryloxy, dialkylamino, alkylarylamino, diarylamino, halogen, cyano, alkoxycarbonyl or aminocarbonyl;

R$^1$ is hydrogen, alkyl optionally substituted with hydroxy, halogen, cyano, alkoxy, aryloxy, dialkylamino, arylalkylamino or diarylamino; or aralkyl;

R$^1$ may be covalently linked to A, R$^5$, R$^6$ and/or R$^7$, in which case —R$^1$—A— or —R$^1$—R$^5$— represents low alkylene, preferentially methylene, ethylene or propylene, unsubstituted or substituted with alkyl, hydroxy, alkoxycarbonyl, alkoxy or dialkylamino, —R$^1$—R$^6$— represents ethylene or propylene, unsubstituted or substituted with alkyl, hydroxy, alkoxy or dialkylamino, and/or —R$^1$—R$^7$— represents methylene, propylene or butylene unsubstituted or substituted with alkyl, hydroxy, alkoxycarbonyl, alkoxy or dialkylamino;

R$^2$ is alkyl optionally substituted with aryl, heteroaryl, alkoxy, aryloxy, cyano, dialkylamino, arylalkylamino, diarylamino or halogen; aryl optionally substituted with alkyl, aryl, heteroaryl, halogen, alkoxy, aryloxy, dialkylamino, alkylarylamino, diarylamino, halogen, cyano, alkoxycarbonyl or aminocarbonyl; heteroaryl optionally substituted with alkyl, aryl, heteroaryl, halogen, alkoxy, aryloxy, dialkylamino, alkylarylamino, diarylamino, halogen, cyano, alkoxycarbonyl or aminocarbonyl; and R$^3$ is cyano, nitro, —CO—R' or —C(OH)—R', R' being alkyl, alkyl substituted with halogen, aryl, aryl substituted with alkyl, aryl, heteroaryl, halogen, alkoxy, aryloxy, dialkylamino, alkylarylamino, diarylamino, halogen, cyano, alkoxycarbonyl or aminocarbonyl or heteroaryl; or —SO$_2$R", R" being alkyl or substituted or unsubstituted aryl.

R$^4$ is hydrogen or COZ, Z being substituted or unsubstituted alkyl, aryl, arylamino or alkylamino; and pharmaceutically acceptable salts thereof;

or of the general formula II

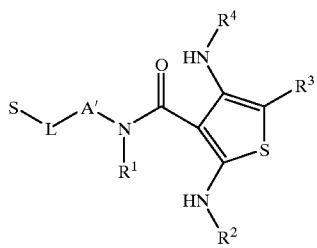

wherein S is a substrate,
L is a chemical bond or a linker,
A' is a chemical bond or a group of formula

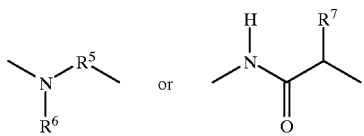

wherein
$R^5$ is alkylene optionally substituted with hydrogen, alkyl, aryl, heteroaryl, alkoxy, aryloxy, cyano, hydroxy, dialkylamino, arylalkylamino, diarylamino or halogen;
$R^6$ is hydrogen, alkyl optionally substituted with hydroxy, halogen, cyano, alkoxy, aryloxy, dialkylamino, arylalkylamino or diarylamino; or aralkyl;
$R^5$ and $R^6$ may be covalently linked to each other by a covalent bond or an additional alkylene group $R^5$, preferentially giving rise to a fragment of the type shown below

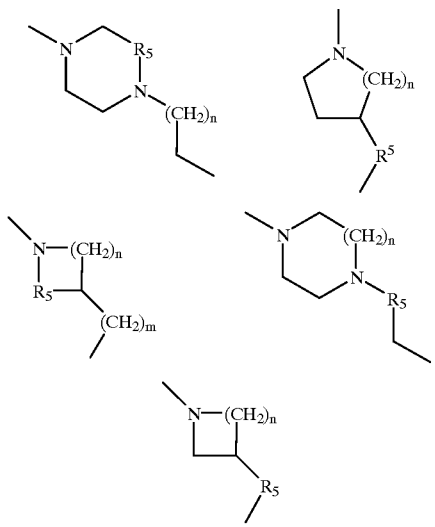

wherein n and m are integers between 0 and 15, preferentially 0 and 3;
$R^7$ is hydrogen, alkyl, alkyl substituted with hydroxy, alkoxy, aryloxy, alkylthio, arylthio, dialkylamino, arylalkylamino or diarylamino; aralkyl, aryl, aryl substituted with alkyl, aryl, heteroaryl, halogen, alkoxy, aryloxy, dialkylamino, alkylarylamino, diarylamino, halogen, cyano, alkoxycarbonyl or aminocarbonyl;

$R^1$ is hydrogen, alkyl optionally substituted with hydroxy, halogen, cyano, alkoxy, aryloxy, dialkylamino, arylalkylamino or diarylamino; or aralkyl;
$R^1$ may be covalently linked to A, $R^5$, $R^6$ and/or $R^7$, in which case —$R^1$—A— or —$R^1$—$R^5$— represents low alkylene, preferentially methylene, ethylene or propylene, unsubstituted or substituted with alkyl, hydroxy, alkoxycarbonyl, alkoxy or dialkylamino, —$R^1$—$R^6$— represents ethylene or propylene, unsubstituted or substituted with alkyl, hydroxy, alkoxy or dialkylamino, and/or —$R^1$—$R^7$— represents methylene, propylene or butylene unsubstituted or substituted with alkyl, hydroxy, alkoxycarbonyl, alkoxy or dialkylamino;
$R^2$ is alkyl optionally substituted with aryl, heteroaryl, alkoxy, aryloxy, cyano, hydroxy, dialkylamino, arylalkylamino, diarylamino or halogen; aryl optionally substituted with alkyl, aryl, heteroaryl, halogen, alkoxy, aryloxy, dialkylamino, alkylarylamino, diarylamino, halogen, cyano, alkoxycarbonyl or aminocarbonyl; heteroaryl optionally substituted with alkyl, aryl, heteroaryl, halogen, alkoxy, aryloxy, dialkylamino, alkylarylamino, diarylamino, halogen, cyano, alkoxycarbonyl or aminocarbonyl; and
$R^3$ is cyano, nitro, —CO—R' or —C(OH)—R', R' being alkyl, alkyl substituted with halogen, aryl, aryl substituted with alkyl, aryl, heteroaryl, halogen, alkoxy, aryloxy, dialkylamino, alkylarylamino, diarylamino, halogen, cyano, alkoxycarbonyl or aminocarbonyl or heteroaryl; or —$SO_2$R", R" being alkyl or substituted or unsubstituted aryl.
$R^4$ is hydrogen or COZ, Z being substituted or unsubstituted alkyl, aryl, arylamino or alkylamino;
and pharmaceutically acceptable salts thereof.

Presently in drug development, high throughput screening is playing a key role. High throughput screening generally incorporates automation and robotics, thus making it possible to screen thousands of compounds in one or more bioassays in a short period of time. This technique has created the need for an automated production of large numbers of different compounds for being screened. A robotic, fully automated system for the production and screening of highly diverse compounds as potential lead-candidates will dramatically speed up the discovery and optimization of new leads for all types of human diseases.

Traditionally, new compounds for lead-discovery or structural analogues for lead-optimization have been synthesized by multiple step linear syntheses. Linear syntheses involve the sequential reactions of several separate reactants in order to obtain the final product. Linear syntheses require the isolation, purification and characterization by spectroscopic and other analytical tools of the intermediate reaction products. Such a linear synthesis is therefore a very time consuming process, which requires a high skill in the synthetic organic chemical art. Since this traditional way of producing compounds is too inefficient for fully exploiting the screening-potential of presently available systems for high throughput screening, synthetic methodology is required, which permits the automated synthesis of large numbers of different compounds.

Parallel solid phase synthesis is today one of the fastest ways of producing arrays of single compounds or arrays of defined mixtures of compounds. However, there are still only few methods available for the parallel solid phase synthesis of organic compounds other than peptides or oligonucleotides. A principal disadvantage associated with peptidic or other bio-oligomeric leads is their low metabolic stability, due to in vivo proteolysis. For this reason, other type of compounds with a higher metabolic stability would be more attractive as leads. Of special interest in this context are small heterocyclic and heteroaromatic compounds, which have been proven to be very useful in many applications. Also as drugs for the treatment of different human metabolic disorders, small heterocyclic compounds have played and are playing a decisive role. For this reason, the solid phase synthesis of heterocyclic compounds is a highly demanded technology, which will be extremely valuable for the fast production of large numbers of potential leads for high volume throughput screening.

Thiophenes are important core structures for biologically active compounds. (S. Gronowitz, Adv. Heterocycl. Chem. 1963, 1, 1; H. D. Hartough, Chem. Heterocycl. Compd. 1952, 3, 1; M. Chaykovsky et al., J. Med. Chem. 1973, 16, 188; A. Michiel van Rhee et. al, J. Med. Chem. 1996, 39, 398–406). The most frequent application of thiophene derivatives (Ullmanns Encyklopädie der Technischen Chemie, 4th Ed., Verlag Chemie, Weinheim 1983, Volume 23, pp 222–223) has been their use as antibiotics, such as cefalonium, and as antiparasitics (tibrofan, atrican, citenazone, nifurzid). Thiophene derivatives have for instance also been used as analgetics (tinoridine, diethylthiambutene), anti-inflammatories (suprofen, tiaprofenic acid), antihelmintics (morantel, pyrantel, thenium chlosylate), anticholinergics (heteronium bromide, oxitefonium bromide, penthienate bromide, tiquizinium bromide, thihexinol methylbromide, thiemonium bromide), antihistaminics (chlorothen, thenalidine, methaphenilene, methapyrilene, thenyldiamine) and antiussives (tipepidine). Thiophene derivatives have been used as anticholesteremics (Bryant, H. U.; Grese, T. A., Can. Pat. Appl. CA 2,117,853 (1995), Chemical Abstracts 1995, 123, 339713y) or for the treatment of disorders associated with amyloidogenic peptides (Lunn, W. H. W., PCT Int. Appl. WO 95 17,095 (1995), Chemical Abstracts 1995, 123, 339715a).

Many more thiophenes than those described so far may be postulated, however, to be potential drug candidates. To achieve the preparation and screening of a large number of compounds with thiophene-core-structure, the present invention provides a solid phase synthesis for thiophenes in which variable substituent groups are independently attached to a common central thiophene ring. The generally recognized advantages of solid phase synthesis are the absence of purification steps of intermediates or the final product, as well as the possibility of automation. Due to these features, a solid phase synthesis of thiophenes dramatically increases the synthesis efficiency for these therapeutically important compounds.

An overall illustration of the solid phase synthesis of thiophenes is shown in reaction Scheme 1.

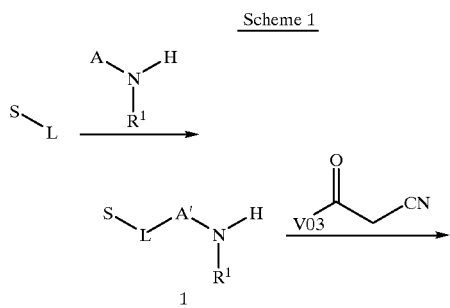

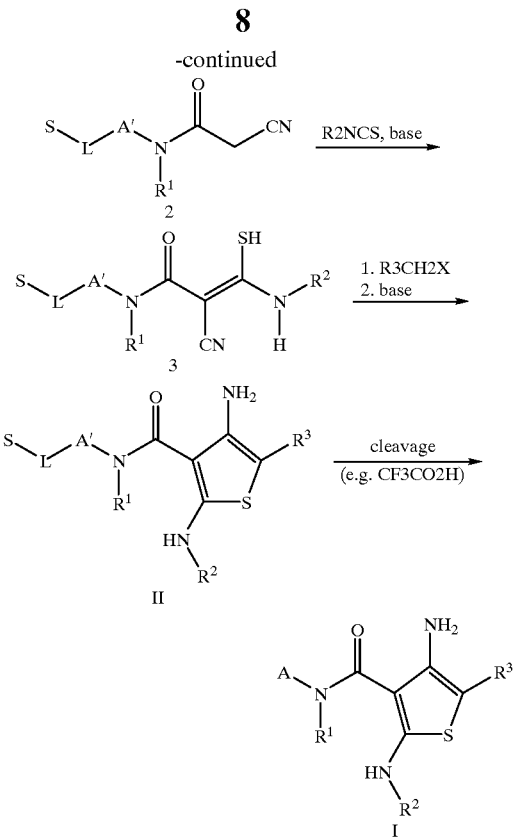

In the following description of this invention, R is intended to be an organic radical. Alkyl is intended to mean lower straight, cyclic, fused or branched alkyl having 1 to 15 carbon atoms, preferentially 1 to 6 carbon atom s. Aryl is intended to mean phenyl or phenyl substituted with alkyl or phenyl, or phenyl fused with cycloalkyl, or polycyclic aromatic systems such as naphthyl, anthracenyl, phenanthrenyl, fluorenyl, etc. Alkylene is intended to mean lower straight, cyclic, fused or branched alkylene having 1 to 15 carbon atoms, preferentially 1 to 6 carbon atoms. Heteroaryl is intended to mean any of the possible isomeric, unsubstituted or alkyl-substituted pyrrolyl, furyl, thienyl, imidazolyl, pyrazolyl, triazolyl, tetrazolyl, oxazolyl, thiazolyl, oxadiazolyl, thiadiazolyl, pyridyl, pyrazinyl, pyrimidinyl and pyridazinyl, as well as the corresponding benzo and dibenzo derivatives or other fused ring-systems thereof. Heteroaryl is also intended to mean the partially or fully hydrogenated derivatives of the heterocyclic systems enumerated above. Alkoxy is intended to mean —O-alkyl and aryloxy is intended to mean —O-aryl. Cyano is intended to mean —CN, hydroxy is intended to mean —OH, amino is intended to mean —$NH_2$ and nitro is intended to mean —$NO_2$. Dialkylamino is intended to mean —N(alkyl)$_2$. Alkylarylamino is intended to mean —N(alkyl)(aryl) and diarylamino is intended to mean —N(aryl)$_2$. Halogen is intended to mean —F, —Cl, —Br and —I. Aralkyl is intended to mean -alkylene-aryl. Alkylthio is intended to mean —S-alkyl and arylthio is intended to mean —S-aryl. Alkoxycarbonyl is intended to mean —CO—O-alkyl and aminocarbonyl is intended to mean —CO—N(alkyl)$_2$, —CO—N(alkyl)(aryl) or —CO—N(aryl)$_2$. Acylamino is intended to mean —N(alkyl)-CO-alkyl or —N(alkyl)-CO-aryl. A leaving group is intended to be a group or atom capable of existing in solution as a negatively charged species, or a positively charged group or atom.

In this synthesis, an organic molecule of the general formula HN($R^6$)—$R^5$—N($R^1$)H or $HO_2C$—CH($R^7$)—N ($R^1$)P, P being a protecting group, is attached to a substrate S via a linker L by well precedented methods, optionally followed by a deprotection step, in such a way, that a free primary or secondary amino group is generated on the support.

The substrate may be any insoluble or partially insoluble material, to which compounds may be covalently attached. Preferentially, the substrates may be selected from the group consisting of polystyrene, polyethylene glycol (PEG), polyethylene glycol attached to polystyrene (e.g. TentaGel), polyamides, polysaccharides and silicates. Depending on the type of substrate chosen, different types of solvents or protecting groups may be used.

Most preferentially, in the case of diamines attached to a substrate, a polystyrene resin or TentaGel resin, covalently attached to a Wang linker (Wang, S. *J. Am.*

*Chem. Soc.* 1973, 95, 1328–1333), may first be treated with phosgene or a phosgene equivalent such as 4-nitrophenyl chloroformate or carbonyldiimidazole, in a suitable solvent such as DCM, THF, toluene, DMF or mixtures thereof, optionally in the presence of a base, such as pyridine, and then with an excess of a diamine such as ethylenediamine, N,N'-dimethylethylenediamine, N,N'-diethylethylenediamine, N,N'-dipropylethylenediamine, N,N'-diisopropylethylenediamine, N,N'-dibutylethylenediamine, N,N'-dihexylethylenediamine, N,N'-dibenzylethylenediamine, N,N'-di(1-hydroxymethyl) propylethylenediamine, piperazine, 2-methylpiperazine, 2,6-dimethylpiperazine, 2,5-dimethylpiperazine, 1,4-diazacycloheptane, 6-hydroxy-1,4-diazacycloheptane, 6-acetoxy-1,4-diazacycloheptane, 1,2-diaminopropane, 1,3-diaminopropane, 1,3-diamino-2-propanol, N,N'-dimethyl-1,3-propanediamine, N,N'-diethyl-1,3-propanediamine, 2,2-dimethyl-1,3-propanediamine, N,N',2-trimethyl-1,3-propanediamine, 1,4-diaminobutane, N,N'-dipropyl-1,4-butanediamine, N,N'-diethylbutane-1,4-diamine, N,N'-dimethyl-2-butene-1,4-diamine, N,N'-diethyl-2-butene-1,4-diamine, N,N'-diethyl-2-butyne-1,4-diamine, 1,5-diaminopentane, 1,3-diaminopentane, 1,2-diaminocyclohexane, 1,3-diaminocyclohexane, 1,4-diaminocyclohexane, 1,3-bis(aminomethyl)cyclohexane, 1,4-bis(aminomethyl)cyclohexane, 4,4'-bipiperidine, 1-[2-(3-pyridylmethylamino)ethyl]-piperazine, 1-(2-aminoethyl) piperazine, 4-aminomethylpiperidine, 3-(4-aminobutyl) piperidine, 5-amino-2,2,4-trimethyl-1-cyclopentanemethylamine, 4,4'-diaminodicyclohexylmethane, o-xylylenediamine, m-xylylenediamine, p-xylylenediamine or isophoronediamine, to give a substrate-bound diamine of the general formula [polystyrene]-[Wang linker]-O—CO—N ($R^6$)—$R^5$—N($R^1$)H. The preparation of such substrate-bound diamines has occasionally been described in literature (e.g. Hiroshige, M.; Hauske, J. R.; Zhou, P. *J. Am. Chem. Soc.* 1995, 117, 11590–11591; Zaragoza, F. *Tetrahedron Lett.* 1995, 36, 8677–8678; Dixit, D. M.; Leznoff, C. C. *Israel J. Chem.* 1978, 17, 248–252; Dixit, D. M.; Leznoff, C. C. *J. Chem . Soc. , Chem. Commun.* 1977, 798–799; Kaljuste, K.; Unden, A. *Tetrahedron Lett.* 1995, 36, 9211–9214).

In the case of protected amino acids attached to a substrate, a polystyrene resin or TentaGel, covalently attached to a Rink linker (H. Rink, *Tetrahedron Lett.* 1987, 28, 3787), may be acylated with a derivative of a side-chain and nitrogen-protected (e.g. FMoc) amino acid, such as FMoc-glycine, FMoc-phenylglycine, FMoc-sarcosine, FMoc-alanine, FMoc-valine, FMoc-norvaline, FMoc-leucine, FMoc-isoleucine, FMoc-norleucine, FMoc-penicillamine, FMoc-arginine, FMoc-asparagine, FMoc-aspartic acid, FMoc-citrulline, FMoc-glutamine, FMoc-glutamic acid, FMoc-proline, FMoc-hydroxyproline, FMoc-phenylalanine, FMoc-tyrosine, FMoc-tryptophan, FMoc-threonine, FMoc-histidine, FMoc-serine, FMoc-cysteine, FMoc-methionine, FMoc-lysine, FMoc-statine or FMoc-omithine, by well established procedures, for example with the in situ generated symmetric anhydride of these amino acid derivatives. Most of the FMoc-amino acids and some of the resulting substrate-bound FMoc-amino acids are commercially available. After this acylation step, the nitrogen protecting group may be removed by well established methods, such as treatment with piperidine in DMF in the case of an FMoc-protecting group, to give a substrate-bound amino acid of the general formula [polystyrene or Tentagel]-[Rink linker]-NH—CO—C($R^7$)H—N($R^1$)H. Also non-natural amino acid derivatives may be attached to a substrate-bound Rink amide linker and converted, by an optional deprotection step, into support-bound amino acids of the type 1 (scheme 1).

The substrate-bound primary or secondary amine 1 may then be acylated with an appropriate cyanoacetic acid derivative of the general structure NC—$CH_2$—COX, X being a leaving group, preferentially with the in situ generated symmetric anhydride (Zaragoza, F. *Tetrahedron Letters.* 1995, 36, 8677–8678). Alternatively, other, in situ generated or isolated derivatives of cyanoacetic acid may be used as acylating reagents, such as the mixed anhydrides derived from alkyl chloroformates and cyanoacetic acid, or the imidazolide or other types of activated esters, such as the N-hydroxybenzotriazolyl ester or N-hydroxysuccinyl ester or other activated esters, obvious to those skilled in the art.

Alternatively, a cyanoacetic acid derivative may be directly reacted with a Rink linker attached to a substrate, to give a derivative of the general formula [substrate]-[Rink linker]-NH—CO—$CH_2$—CN. This corresponds to the case, where A' (scheme 1) is a chemical bond and A is hydrogen.

The resulting, resin bound cyanoacetamide 2 may then be treated with an excess of an aromatic or aliphatic isothiocyanate of the general structure $R^2$—NCS in an appropriate solvent such as DMF or THF, in the presence of a base, preferentially 1,8-diazabicyclo[5.4.0]undec-7-ene (DBU).

The group $R^2$ may be straight or branched alkyl groups, such as methyl, ethyl, propyl, isopropyl, butyl, including n-butyl, sec-butyl, iso-butyl, tert-butyl, pentyl, hexyl, heptyl, octyl, etc., and their variants, straight or branched alkylene chains such as methylene, 1,2-ethylene, 1,1-ethylene, propylene, etc. linked to cycloalkyl groups, substituted or unsubstituted aryl groups such as phenyl, naphthyl, biphenylyl or monovalent radicals of substituted or unsubstituted heterocycles and heteroaromatics such as pyridyl, thienyl, pyrrolyl, furyl, piperidinyl, pyrrolidinyl, etc. Additionally, $R^2$ may be substituted or unsubstituted aryl groups or substituted or unsubstituted heterocycles or heteroaromatics. All these groups may also be substituted with functional groups such as F, Cl, Br, I, $CONR_2$, $CO_2R$, CN, $NO_2$, SR, SOR, $SO_2R$, $SO_2NR_2$, OR or $NR_2$, R being low alkyl or aryl.

The resulting intermediate product 3 may then be alkylated at the sulphur atom with an alkylating agent of the general structure X—$CH_2$—$R^3$, X being a leaving group for nucleophilic displacement and $R^3$ being an electron withdrawing group such as an acyl group R'CO—, R' being substituted or unsubstituted alkyl, substituted or unsubstituted heteroaryl, substituted or unsubstituted aryl, a cyano group, a formyl group, a nitro group, a sulfonyl group R"$SO_2$—, R" being substituted or unsubstituted alkyl or substituted or unsubstituted aryl, an aminocarbonyl group —CON(R)$_2$, R being independently low alkyl or aryl, an alkoxycarbonyl group or an aryl group substituted with one or more electron withdrawing substituents, in an appropriate solvent such as DMF, DCM, acetonitrile or THF, either under neutral or acidic conditions. The leaving group X may be, for instance Cl—, Br—, I—, —OCOR, —OH$_2^+$ or —OSO$_2$R". When this alkylation is completed, the resulting, S-alkylated intermediate may be treated with a base, such as DBU, guanidines, potassium hexamethyldisilazide or alcoholates, in an appropriate solvent such as DMF, THF, alcoholes or acetonitrile, thereby inducing a Thorpe-Ziegler-cyclization to the substrate-bound thiophene II. The choice of base and solvent may depend on the type of substrate used.

Cleaving of the linker of the substrate-bound thiophene II may release the 3-aminothiophene derivative I into solution. Cleavage conditions will depend upon the type of substrate and linker chosen. E.g., in the case of a polystyrene resin with a Wang linker or a Rink linker, treatment of the support-bound thiophene II with neat TFA or TFA/DCM mixtures may lead to a cleavage of the linker.

Alternatively, further chemical transformations may be carried out with the substrate-bound thiophene II. These comprise the acylation at the 3-amino group with e.g. carboxylic acid derivatives, sulfonic acid derivatives, isocyanates or isothiocyanates. In the case where $R^3$=—COR', R' being hydrogen or substituted or unsubstituted alkyl or aryl, the reduction of the keto group in the resin bound thiophene II may yield a primary or secondary alcohol, which may be cleaved from the support or first acylated with carboxylic acid derivatives, sulfonic acid derivatives, isocyanates or isothiocyanates either at the hydroxy group or at the amino group, the site of acylation depending on the precise reaction conditions, and then cleaved from the support. Alternatively, in the case where $R^3$=—COR', —COR', R' being hydrogen or substituted or unsubstituted alkyl or aryl, the keto- or formyl-group of the substrate-bound thiophene II may be chemically transformed in numerous ways, obvious to those skilled in the art. It may be converted into a hydrazone or an oxime, it may be reductively aminated or reacted with organometallic reagents or condensed with CH-acidic compounds such as nitroalkanes, 1,3-dicarbonyl compounds, malononitrile, disulfonyl methanes, etc. Each of these reactions may be performed by conventional means, readily apparent to those skilled in the art.

Using this synthetic method, arrays of thiophene derivatives II or I may be constructed with the help of a device for parallel solid phase synthesis. This may be either the pin method developed by Geysen et al. (*J. Immunol. Meth.* 1987, 102, 259–274) or a device with several reactors for solid phase synthesis (containers with a permeable wall), which permits the automated addition of reagents and solvents, as well as the removal of the solvents from the reactors by simultaneous or individual application of a pressure difference between the inside and the outside of the permeable wall of the reactors.

Such an array may be prepared on a multiple organic synthesizer (e.g. "ACT 496" of "Advanced ChemTech") by individually reacting under the conditions specified below different amines attached to a substrate and located in individual containers, first with a cyanoacetic acid derivative and then with different isothiocyanates of the general structure $R^2$—NCS in the presence of a base. The resulting intermediates 3 may then be alkylated at the sulphur atom with an alkylating agent of the general structure X—CH$_2$—$R^3$, X being a leaving group for nucleophilic displacement and $R^3$ being an electron withdrawing group, either under neutral or acidic conditions, to give, after treatment with DBU and optional cleavage from the support, an array of different thiophene derivatives II.

The present invention also permits the synthesis of arrays of mixtures of 3-aminothiophene derivatives. This can be achieved either by the "split and mix" method (Sepetov, N. F., Krchnák, V., Stankova, M., Wade, S., Lam, K. S., and Lebl *Proc. Natl. Acad. Sci. USA* 1995, 92, 5426–5430) or by using mixtures of the corresponding reagents.

By virtue of the present invention basically two different types of arrays of thiophenes I or II may be constructed: fully combinatorial arrays (FCA) and not-fully combinatorial arrays (NFCA).

By FCA we refer to arrays of substituted thiophenes, in which all the possible combinations of a set of selected building blocks (R-groups) are realized. As an example, a FCA of N thiophenes may be prepared by selecting n diamines, m isothiocyanates and p haloketones so that n×m×p=N, and synthesizing all the possible combinations of diamine/isothiocyanate/haloketone. The selection of building blocks may be done with regard to the expected properties of the members of the array.

By NFCA we refer to arrays of substituted thiophenes, in which only a selection of the possible combinations of a set of selected building blocks is realized. As an example, a NFCA of N thiophenes may be prepared by first selecting n diamines, m isothiocyanates and p haloketones so that n×m×p>N. Then a selection of N thiophenes from all the n×m×p theoretically possible thiophenes is done by grouping all the n×m×p possible thiophenes into N groups of thiophenes with similar expected properties and selecting from each of these groups one thiophene, which is then synthesized. The selection of building blocks and of thiophenes may be done with regard to the expected properties of the members of the array.

For the preparation of such arrays of compounds, the exact positions of the is substrate does, by itself, not give any structural information about the compound prepared on this particular batch of substrate. For this reason, the spatial arrangement of the substrate is irrelevant. Structural information will be accessible from the records of the sequences of reagents added to each batch of substrate. In every step of the preparation of a FCA or a NFCA, the exact location of one substrate-container within the array of containers and the structure of the different reagents added to this container is recorded, so that the precise structure of the thiophene resulting from one given container can always be deduced.

The resulting arrays of 2-aminothiophenes may then be screened by comparing the individual thiophenes in terms of their ability to bind to a particular receptor or to induce a particular biological process or to catalyze a biological or chemical reaction. This can be achieved basically in two different ways. One possibility may be the screening of the substrate-bound thiophenes II, e.g. against a soluble receptor. This could for instance be a radioactively labelled peptide or enzyme, which would easily permit to determine the binding-strength of a given substrate-bound thiophene II to this peptide by washing away the excess of radioligand used and determining the remaining radioactivity of each substrate-bound thiophene II-peptide complex. Alternatively, as a further example, catalytic activity of the different substrate-bound thiophenes II for a given biological process or a chemical reaction may be measured by comparing the speed at which this biological process or a chemical reaction takes place in the presence and in the absence of a given substrate-bound thiophene II.

The second option for screening may consist in screening the thiophenes I, after having cleaved the linker of the substrate-bound thiophenes II and using appropriately charged and indexed Microtiter plates of similar multiwell arrangements, in solution against an optionally substrate-bound receptor or enzyme. The screening of soluble small molecules is conventional and well known. Typically, radioassays are being used, in which the competitive binding of the radiolabelled, natural ligand of a given receptor and the compound to be tested for binding to this receptor is investigated.

An example would be a screening against the cholecystokinine receptors, which are widely distributed throughout the central and peripheral nervous system and mediate numerous physiological responses. Crude membrane homogenates may be prepared according to the procedure described by Chang et al. (*Proc. Natl. Acad. Sci.* 1986, 4923–4926) and radiolabelled cholecystokinine can be purchased from New England Nuclear, Massachusetts, U.S.A. Other examples will be readily apparent to those skilled in the arts of physiology, biology and biotechnology. These could for instance be the somatostatine receptors, the glucagon receptors, the insulin receptor, the opiate receptors, the dopamine receptors, the acetylcholine receptors, the histamine receptors, etc.

Alternatively, functional or other assays may be used, in which for example the biological response of a cell or a genetically modified or unmodified organism is measured as a function of the amount of test-substance added to this organism. As a further example, the catalytic activity of the different thiophenes I for a given biological process or a chemical reaction may be measured by comparing the speed at which this biological process or a chemical reaction takes place in the presence and in the absence of a given thiophene I.

The methods described above may be used to prepare and screen large numbers of compounds in a reasonable amount of time. Synthesis may be combined with screening in various different ways to screen compounds in unusually large arrays.

References

1. Gallop, M. A.; Barrett, R. W.; Dower, W. J.; Fodor, S. P. A.; Gordon, E. M. *J. Med. Chem.* 1994, 37, 1233–1251.
2. Gordon, E. M.; Barrett, R. W.; Dower, W. J.; Fodor, S. P. A.; Gallop, M. A. *J. Med. Chem.* 1994, 37, 1385–1401.
3. Terrett, N. K.; Gardner, M.; Gordon, D. W.; Kobylecki, R. J.; Steele, J. *Tetrahedron.* 1995, 51, 8135–8173.
4. Lebl, M.; Krchnák, V.; Sepetov, N. F.; Kocis, P.; Patek, M.; Flegelova, Z.; Ferguson, R.; Lam, K. S. *Journal Of Protein Chemistry.* 1994, 13, 484–486.
5. Sepetov, N. F.; Krchnák, V.; Stankova, M.; Wade, S.; Lam, K. S.; Lebl, M. *Proc. Natl. Acad. Sci. USA* 1995, 92, 5426–5430.
6. Liskamp, R. M. *J. Angew. Chem. Int Ed. Engl.* 1994, 33, 633–636.
7. Houghten, R. A.; Kay, B. K.; Madden, D.; Krchnák, V.; Lebl, M.; Chabala, J. C.; Kauffman, S. *Perspectives in Drug Discovery and Design* 1994, 2, 249–325.
8. Seligmann, B.; Abdul-Latif, F.; Al-Obeidi, F.; Flegelova, Z. *European Journal Of Medicinal Chemistry* 1995, 30, 319–335.
9. Baldwin, J. J.; Burbaum, J. J.; Henderson, I.; Ohlmeyer, M. H. J. *J. Am. Chem. Soc.* 1995, 117, 5588–5589.
10. Jung et al., "Multiple Peptide Synthesis Methods and their Applications", *Angew. Chem. Int. Ed. Engl.* 1992, 31, 367–383.
11. Laliberté, R.; Médawar, G. *Canadian Journal of Chemistry* 1970, 48, 2709–2717.
12. Gewald, K.; Hentschel, M. *Journal für Praktische Chemie* 1976, 318, 343–346.
13. Chiba, T.; Sato, H.; Kato, T. *Chemical And Pharmaceutical Bulletin.* 1982, 30, 3548–3554.
14. Gewald, K.; Hain, U.; Schmidt, M. *Journal für Praktische Chemie* 1986, 328, 459–464.
15. Augustin, M.; Dölling, W. *Journal für Praktische Chemie* 1982, 324, 322–328.
16. Augustin, M.; Rudorf, W.-D.; Schmidt, U. *Tetrahedron* 1976, 32, 3055–3061.
17. J. A. Ellman, Solid phase and combinatorial synthesis of benzodiazepine compounds on a solid support, U.S. Pat. No. 5,288,514; Feb. 22, 1994.
18. Dolman, H. and Kuipers, J. Preparation of thio compounds having fungicidal activity. *Chemical Abstracts* 1988, 109, 110245k. Eur. Pat. Appl. EP 234,622
19. Briel, D., Wagner, G., and Lohmann, D. Preparation of 5-substituted 3-aminothiophene-4-nitriles. *Chemical Abstracts* 1990, 113, 131988c, Ger.(East) DD 275,870
20. Laliberté, R. Antibacterial 5-aminothieno[3,4-d]pyridmidine-4(3H)-one derivatives. *Chemical Abstracts* 1972, 76, 140867g, U.S. Pat. No. 3,644,357; Ayerst, McKenna and Harrison Ltd.
21. Laliberté, R. Amebicidal 2,4-diamino-3-thiophenecarboxylic acid. *Chemical Abstracts* 1970, 73, 3785c, U.S. Pat. No. 3,506,669; American Home Products Corp.

EXAMPLES

Synthesis of [2-phenylamino-4-amino-5-(2,4-dichlorobenzoyl)thiophen-3-yl]piperazin-1-ylmethanone trifluoroacetate To a suspension of Wang resin (45.0 g, 42.3 mmol, Novabiochem, loading: 0.94 mmol/g) in DCM (600 mL) first pyridine (52 mL) and then a solution of 4-nitrophenyl chloroformate (43.0 g, 231 mmol) was added. After shaking for 3 h at room temperature the mixture was filtered, the resin was washed with DCM (5×300 mL) and then added to a cold solution of piperazine (38.2 g, 444 mmol) in DMF (600 mL). The resulting mixture was stirred for 13 h, filtered and the resin was washed extensively with DMF, DCM and methanol. After drying approx. 45 g of the carbamate-resin 1 was obtained.

To the DCM-swollen resin 1 (0.20 g, approx. 0.2 mmol) a solution of cyanoacetic acid (0.17 g, 2.02 mmol) in DMF (1.5 mL) and DCM (1.5 mL) was added, followed by the addition of diisopropylcarbodiimide (0.14 mL, 0.89 mmol). The resulting mixture was shaken for 3 h, filtered, washed with DMF (3×6 mL) and treated once more with cyanoacetic acid and diisopropylcarbodiimide as above for 3 h, to give, after washing with DMF, the resin bound cyanoacetamide 2.

A solution of phenyl isothiocyanate (0.24 mL, 2.02 mmol) in DMF (2 mL) was added to the resin 2, followed by the addition of DBU (0.7 mL). The mixture was shaken for 18 h, filtered, and the resin was washed extensively with DMF.

A solution of 2,4-dichlorophenacyl chloride (0.48 g, 2.16 mmol) in DMF (2 mL) was then added to the resin and the mixture was shaken for 20 h. After filtration and washing with DMF, the resin was suspended in a mixture of DBU (1 mL) and DMF (2 mL) and shaken for 20 h.

After filtration the resin was carefully washed with DMF, methanol, DCM and 10% AcOH in DCM. It was then suspended in DCM (2 mL) and TFA (2 mL) and shaken for 3 h. Filtration, washing with DCM and concentration of the filtrates yielded 145 mg of [2-(phenylamino)4-amino-5-(2,4-dichlorobenzoyl)thiophen-3-yl]piperazin-1-ylmethanone trifluoroacetate as an oil.

HPLC (Lichrosorb RP 18, acetonitrile/water gradient, monitored at 254 nm): elution at 21.7 min, 91% pure. $^1$H NMR (400 MHz, DMSO-$d_6$) δ 3.10–3.20 (s, br, 4H), 3.55–3.80 (m, 4H), 7.12 (t, J=8.0 Hz, 1H), 7.22 (d, J=8.0 Hz, 2H), 7.33 (t, J=8.0 Hz, 2H), 7.40 (d, J=8.0 Hz, 1H), 7.47 (dd, J=8.0, 2.0 Hz, 1H), 7.69 (d, J=2.0 Hz, 1H), 8.9 (s, br, 2H), 9.50 (s, 1H); $^{13}$C NMR (100 MHz, DMSO-$d_6$) δ 42.62 (t), 96.63 (s), 104.05 (s), 115.5 (q, J=291 Hz, $CF_3$), 121.15 (d), 124.76 (d), 127.45 (d), 129.32 (d), 129.49 (d), 129.55 (d), 130.72 (s), 134.31 (s), 139.07 (s), 140.25 (s), 156.01 (s), 157.90 (s), 158.09 (q, J=37 Hz, $CF_3$-$CO_2$), 162.85 (s), 180.70 (s); IR (KBr): ν 3445, 3000, 2600, 2500, 1690 cm$^{-1}$; MS m/z 477, 475 (MH$^+$); HRMS calcd. for $C_{22}H_{20}Cl_2N_4O_2S$: 474.0681. Found: 474.0684.

Automated Synthesis of an Array of Eighty Different Thiophenes

An array of eighty different thiophenes has been prepared in the following way:

Into eighty reactors of the multiple organic synthesizer "ACT 496" of "Advanced ChemTech" the four diamines piperazine, N,N'-dibenzylethylenediamine, 1,4-diazacycloheptane and 1,2-diaminocyclohexane, previously attached to a Wang resin via a carbamate-group, were equally distributed [100 mg (approx. 0.1 mmol) of each resin-bound diamine into each of twenty reactors]. Then all the samples of resin-bound diamine were acylated with cyanoacetic acid anhydride (2×3 h) as described above. When this acylation was completed, the resulting resin-bound cyanoacetamides were reacted with five different isothiocyanates (3-methoxypropyl isothiocyanate, 3-(trifluoromethyl)phenyl isothiocyanate, 2,3-dichlorophenyl isothiocyanate, 4-diethylaminophenyl isothiocyanate and 1-naphthyl isothiocyanate) in the presence of DBU (as described above) in such a way, that each of the four different cyanoacetamides were treated with all of the five isothiocyanates. After this reaction, the resulting, resin-bound intermediates 3 were treated with four different alpha-bromoketones (2,5-dimethoxyphenacyl bromide, 1,1,1-trifluoro-3-bromo-2-propanone, 4-phenylphenacyl bromide and 2-bromoacetylnaphthalene) in 10% AcOH in DMF in such a way, that all possible combinations of diamine-isothiocyanate-bromoketone were realized. After cyclization with DBU, the resulting resin-bound thiophenes were cleaved from the resin by treatment with 60% TFA in DCM (5 h), yielding an array of eighty different thiophenes in purities of 30→90% (HPLC).

Following the procedure given above, the following thiophene derivatives I have been prepared:

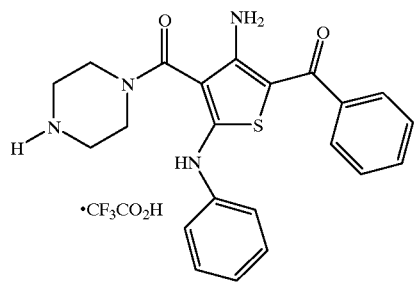

(2-phenylamino-4-amino-5-benzoylthiophen-3-yl) piperazin-1-ylmethanone trifluoroacetate HPLC (Lichrosorb RP 18, acetonitrile/water gradient, monitored at 254 nm): elution at 17.9 min, 76% pure. $^1$H NMR (400 MHz, DMSO-$d_6$) δ 3.03–3.25 (m, 4H), 3.50–3.80 (m, 4H), 7.11 (t, J=7.4 Hz, 1H), 7.31 (d, J=7.4 Hz, 2H), 7.32–7.38 (m, 2H), 7.40–7.51 (m, 3H), 7.61 (dd, J=7.4, 1.8 Hz, 2H), 8.80–9.30 (m, 2H), 9.39 (s, 1H); $^{13}$C NMR (100 MHz, DMSO-$d_6$) δ 40.03 (t), 42.66 (t), 95.58 (s), 104.49 (s), 115.5 (q, J=291 Hz), 120.59 (d), 124.25 (d), 126.82 (d), 128.28 (d), 129.40 (d), 130.19 (d), 140.54 (s), 141.46 (s), 156.09 (s), 156.87 (s), 158.47 (q, J=37 Hz), 163.15 (s), 184.48 (s); IR (KBr): ν 3450, 2994, 2709, 2504, 1674, 1448 cm$^{-1}$; MS m/z 407 (MH$^+$), 321. HRMS calcd. for ($C_{22}H_{22}N_4O_2S$): 406.1459. Found: 406.1464.

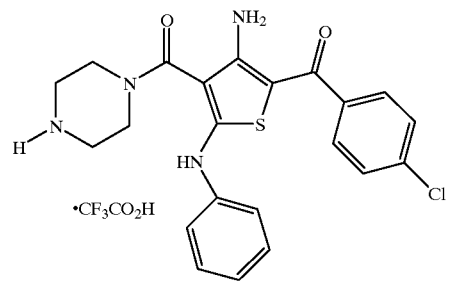

[2-phenylamino-4-amino-5-(4-chlorobenzoyl)-thiophen-3-yl]piperazin-1-ylmethanone trifluoroacetate HPLC (Lichrosorb RP 18, acetonitrile/water gradient, monitored at 254 nm): elution at 21.3 min, 63% pure. $^1$H NMR (400 MHz, DMSO-$d_6$) δ 3.10–3.25 (s, br, 4H), 3.55–3.80 (m, 4H), 7.05–7.65 (m, 7H), 7.94 (d, J=7.5 Hz, 2H).

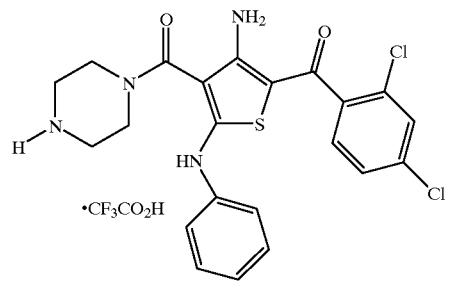

[2-phenylamino-4-amino-5-(2,4-dichlorobenzoyl)-thiophen-3-yl]piperazin-1-ylmethanone trifluoroacetate HPLC (Lichrosorb RP 18, acetonitrile/water gradient, monitored at 254 nm): elution at 21.7 min, 91% pure. $^1$H NMR (400 MHz, DMSO-$d_6$) δ 3.10–3.20 (s, br, 4H), 3.55–3.80 (m, 4H), 7.12 (t, J=8.0 Hz, 1H), 7.22 (d, J=8.0 Hz, 2H), 7.33 (t, J=8.0 Hz, 2H), 7.40 (d, J=8.0 Hz, 1H), 7.47 (dd, J=8.0, 2.0 Hz, 1H), 7.69 (d, J=2.0 Hz, 1H), 8.9 (s, br, 2H), 9.50 (s, 1H); $^{13}$C NMR (100 MHz, DMSO-$d_6$) δ 42.62 (t), 96.63 (s), 104.05 (s), 115.5 (q, J=291 Hz), 121.15 (d), 124.76 (d), 127.45 (d), 129.32 (d), 129.49 (d), 129.55 (d), 130.72 (s), 134.31 (s), 139.07 (s), 140.25 (s), 156.01 (s), 157.90 (s), 158.09 (q, J=37 Hz), 162.85 (s), 180.70 (s); IR (KBr): ν 3445, 3000, 2600, 2500, 1690 cm$^{-1}$; MS m/z 477, 475 (MH$^+$); HRMS calcd. for ($C_{22}H_{20}Cl_2N_4O_2S$): 474.0681. Found: 474.0684.

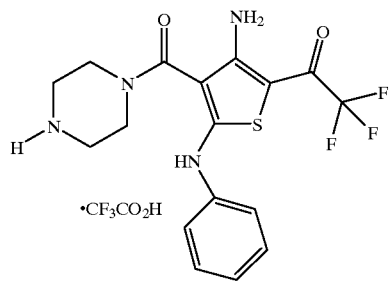

(5-trifluoroacetyl-2-phenylamino-4-aminothiophen-3-yl) piperazin-1-ylmethanone trifluoroacetate HPLC (Lichrosorb RP 18, acetonitrile/water gradient, monitored at 254 nm): elution at 8.8 min, 90% pure. $^1$H NMR (400 MHz, DMSO-$d_6$) δ 3.10–3.25 (s, br, 4H), 3.55–3.90 (m, 4H), 5.61 (s, 1H), 7.14 (t, J=7.8 Hz, 1H), 7.37 (t, J=7.8 Hz, 2H), 7.55 (d, J=7.8 Hz, 2H), 9.02 (s, br, 2H), 10.65 (s, 1H); IR (KBr): ν 2944, 2480, 1783, 1500 cm$^{-1}$; MS m/z 399 (MH$^+$).

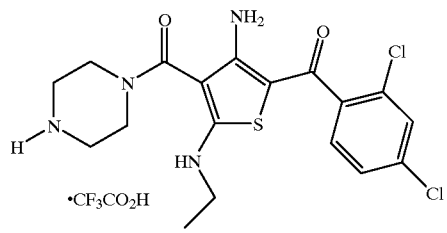

[2-ethylamino-4-amino-5-(2,4-dichlorobenzoyl)-thiophen-3-yl]piperazin-1-ylmethanone trifluoroacetate HPLC (Lichrosorb RP 18, acetonitrile/water gradient, monitored at 254 nm): elution at 18.5 min, 74% pure. $^1$H NMR (400 MHz, DMSO-$d_6$) δ 1.10 (t, J=6.9 Hz, 3H), 3.02–3.25 (m, 4H), 3.45–3.95 (m, 6H), 7.42 (d, J=8.1 Hz, 1H), 7.50 (dd, J=8.1, 1.5 Hz, 1H), 7.59 (m, 1H), 7.70 (d, J=1.5 Hz, 1H), 8.90–9.30 (m, 2H); $^{13}$C NMR (100 MHz, DMSO-$d_6$) δ 14.02 (q), 41.53 (t), 42.56 (t), 97.5 (q, J=291 Hz), 127.46 (d), 128.16 (s), 128.86 (s), 129.23 (d), 129.59 (d), 130.77 (s), 134.07 (s), 139.51 (s), 156.91 (s), 158.46 (q, J=37 Hz), 163.46 (s), 163.79 (s), 179.46 (s); IR (KBr): ν 2980, 2492, 1674, 1621, 1586, 1488 cm$^{-1}$; MS m/z 429, 427 (MH$^+$), 341.

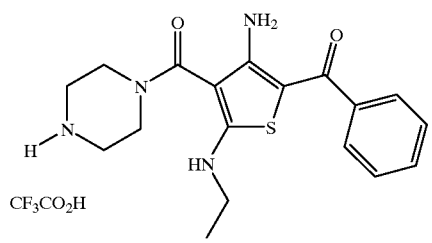

(2-ethylamino-4-amino-5-benzoylthiophen-3-yl) piperazin-1-ylmethanone trifluoroacetate HPLC (Lichrosorb RP 18, acetonitrile/water gradient, monitored at 254 nm): elution at 14.2 min, 29% pure. $^1$H NMR (400 MHz, DMSO-$d_6$) δ 1.04 (t, J=7.0 Hz, 3H), 3.05–3.25 (m, 6H), 3.45–3.90 (m, 4H), 8.54 (m, 1H), 8.90 (m, 2H).

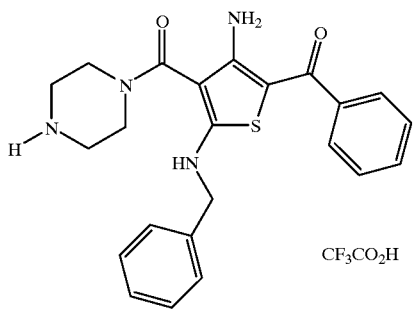

(2-benzylamino-4-amino-5-benzoylthiophen-3-yl) piperazin-1-ylmethanone trifluoroacetate HPLC (Lichrosorb RP 18, acetonitrile/water gradient, monitored at 254 nm): elution at 18.1 min, 38% pure. $^1$H NMR (400 MHz, DMSO-$d_6$) δ 3.10–3.20 (m, 4H), 3.45–3.80 (m, 4H), 4.34 (s, br, 2H), 7.20–7.55 (m, 10H), 8.90 (s, br, 2H).

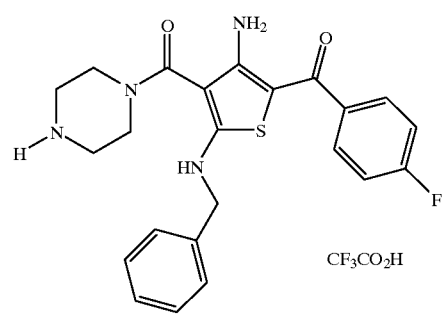

[2-benzylamino-4-amino-5-(4-fluoro benzoyl)-thiophen-3-yl]piperazin-1-ylmethanone trifluoroacetate $^1$H NMR (400 MHz, DMSO-$d_6$) δ 3.05–3.20 (m, 4H), 3.52–3.76 (m, 4H), 4.35 (s, br, 2H), 7.23–7.38 (m, 7H), 7.61 (m, 2H), 8.95 (s, br, 2H).

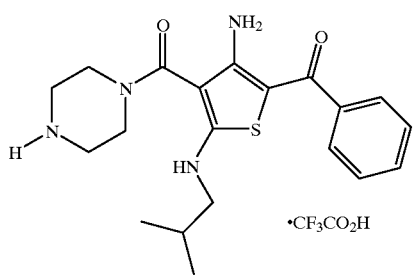

(2-isobutylamino-4-amino-5-benzoylthiophen-3-yl) piperazin-1-ylmethanone trifluoroacetate HPLC (Lichrosorb RP 18, acetonitrile/water gradient, monitored at 254 nm): elution at 17.5 min, 47% pure. $^1$H NMR (400 MHz, DMSO-$d_6$) δ 0.80–0.90 (m, 6H), 1.92 (m, 1H), 3.05–3.25 (m, 6H), 3.50–3.90 (m, 4H), 7.42–7.62 (m, 5H), 8.90 (m 2H).

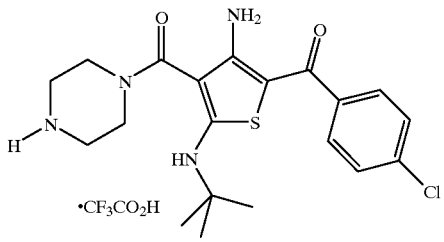

[2-tert-butylamino-4-amino-5-(4-chlorobenzoyl)-thiophen-3-yl]piperazin-1-ylmethanone trifluoroacetate HPLC (Lichrosorb RP 18, acetonitrile/water gradient, monitored at 254 nm): elution at 20.8 min, 30% pure. $^1$H NMR (400 MHz, DMSO-$d_6$) δ 1.32 (s, 9H), 3.10–3.20 (s, br, 4H), 3.55–3.80 (m, 4H), 7.53 (d, J=8.0 Hz, 2H), 7.64 (d, J=8.0 Hz, 2H), 8.90 (m, 2H).

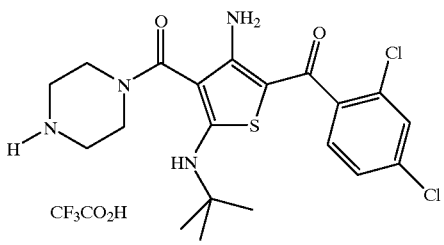

[2-(tert-butylamino)-4-amino-5-(2,4-dichlorobenzoyl)-thiophen-3-yl]piperazin-1-ylmethanone trifluoroacetate HPLC (Lichrosorb RP 18, acetonitrile/water gradient, monitored at 254 nm): elution at 19.2 min, 80% pure. $^1$H NMR (400 MHz, DMSO-$d_6$) δ 1.31 (s, 3H), 3.05–3.20 (m, 4H), 3.40–3.68 (m, 4H), 7.21 (s, br, 1H), 7.46 (d, J=7.5 Hz, 1H), 7.52 (dd, J=7.5, 1.5 Hz, 1H), 7.72 (d, J=1.5 Hz, 2H), 9.00 (m, 2H).

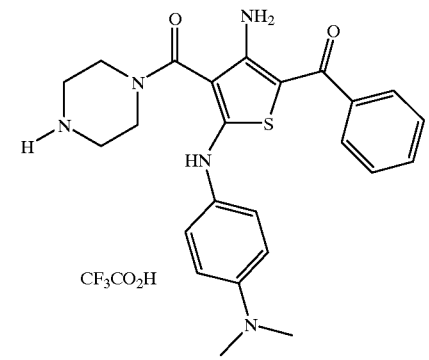

[2-(4-dimethylaminophenylamino)-4-amino-5-benzoyl)-thiophen-3-yl]piperazin-1-ylmethanone trifluoroacetate HPLC (Lichrosorb RP 18, acetonitrile/water gradient, monitored at 254 nm): elution at 10.8 min, 41% pure. $^1$H NMR (400 MHz, DMSO-$d_6$) δ 2.95 (s, 6H), 3.10–3.20 (m, 4H), 3.55–3.80 (m, 4H), 6.94 (d, J=8.0 Hz, 2H), 7.18 (d, J=8.0 Hz, 2H), 7.42 (m, 3H), 7.52 (m, 2H), 8.90 (s, br, 2H), 9.20 (s, 1H); MS m/z 450 (MH$^+$), 317.

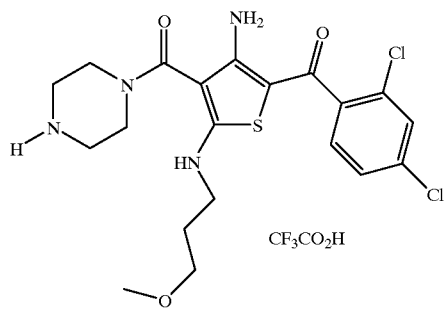

[2-(3-methoxypropylamino)4-amino-5-(2,4-dichlorobenzoyl)-thiophen-3-yl]piperazin-1-ylmethanone trifluoroacetate HPLC (Lichrosorb RP 18, acetonitrile/water gradient, monitored at 254 nm): elution at 15.3 min, 82% pure. $^1$H NMR (400 MHz, DMSO-$d_6$) δ 1.72 (m, 2H), 3.08 (m, 2H), 3.18 (s, br, 5H), 3.30 (s, br, 4H), 3.45–3.71 (m, 4H), 7.41 (dd, J=8.0, 1.5 Hz, 1H), 7.53 (dd, J=8.0, 1.0 Hz, 1H), 7.59 (m, 1H), 7.70 (m, 1H), 8.95 (s, br, 2H).

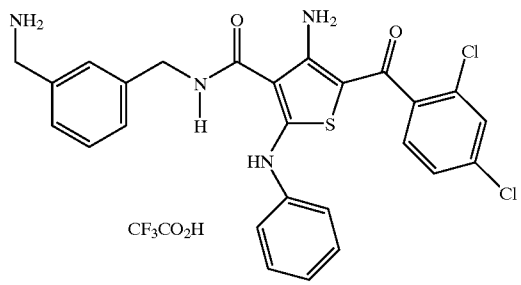

2-phenylamino-4-amino-5-(2,4-dichlorobenzoyl)thiophene-3-carboxylic acid 3-(aminomethyl)benzylamide trifluoroacetate HPLC (Lichrosorb RP 18, acetonitrile/water gradient, monitored at 254 nm): elution at 25.1 min, 59% pure. $^1$H NMR (400 MHz, DMSO-$d_6$) δ 4.00 (m, 2H), 4.45 (m, 2H), 7.05–7.70 (m, 12H), 8.20 (m, 3H).

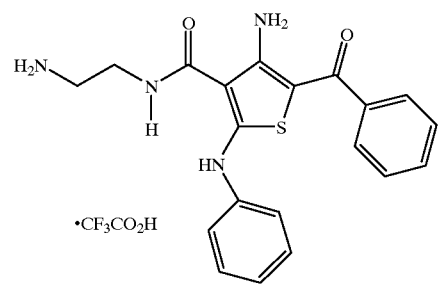

2-phenylamino-4-amino-5-benzoylthiophene-3-carboxylic acid 2-aminoethylamide trifluoroacetate HPLC (Lichrosorb RP 18, acetonitrile/water gradient, monitored at 254 nm): elution at 71.3 min, 43% pure.

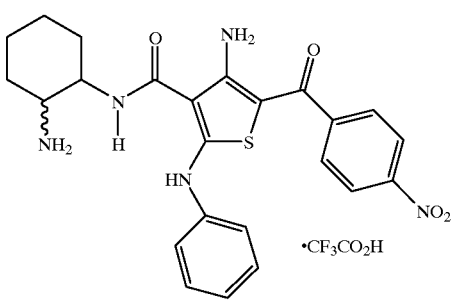

2-phenylamino-4-amino-5-(4-nitrobenzoyl)thiophene-3-carboxylic acid 2-aminocyclohexylamide trifluoroacetate HPLC (Lichrosorb RP 18, acetonitrile/water gradient, monitored at 254 nm): elution at 15.5 min and 23.4 min, two diastereomers, 58% pure.

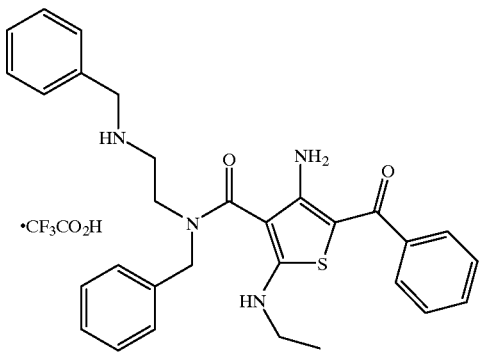

2-ethylamino-4-amino-5-benzoylthiophene-3-carboxylic acid benzyl-2-(benzylamino)ethylamide trifluoroacetate HPLC (Lichrosorb RP 18, acetonitrile/water gradient, monitored at 254 nm): elution at 25.1 min, 27% pure.

CONCLUSION

The above description is illustrative and not restrictive. Various modifications and variations of the invention will become apparent to those of skill in the art upon review of this disclosure. Merely by way of example a wide variety of process times, reaction temperature as well as different ordering of certain processing steps may be utilized. The scope of the invention should, therefore, be determined, not with reference to the above description, but instead should be determined with reference to the appended claims along with their full scope of equivalents.

What is claimed is:

1. A method for preparing a compound of formula I

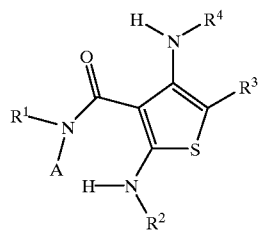

wherein

A is a hydrogen atom or a group of formula

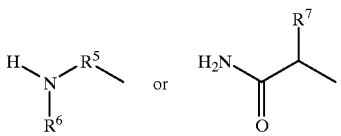

wherein $R^5$ is alkylene optionally substituted with hydrogen, alkyl, aryl, heteroaryl, alkoxy, aryloxy, cyano, hydroxy, dialkylamino, arylalkylamino, diarylamino or halogen;

$R^6$ is hydrogen, alkyl optionally substituted with hydroxy, halogen, cyano, alkoxy, aryloxy, dialkylamino, arylalkylamino or diarylamino; or aralkyl;

$R^5$ and $R^6$ may be covalently linked to each other by a covalent bond or an additional alkylene group $R^5$, thereby giving rise to a fragment of the type shown below

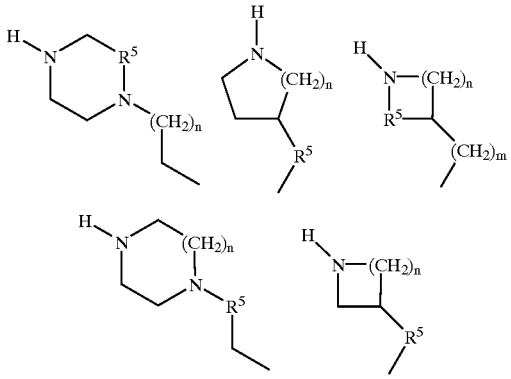

wherein n and m are integers between 0 and 15;

$R^7$ is hydrogen, alkyl, alkyl substituted with hydroxy, alkoxy, aryloxy, alkylthio, arylthio, dialkylamino, arylalkylamino or diarylamino; aralkyl, aryl, aryl substituted with alkyl, aryl, heteroaryl, halogen, alkoxy, aryloxy, dialkylamino, alkylarylamino, diarylamino, halogen, cyano, alkoxycarbonyl or aminocarbonyl;

$R^1$ is hydrogen, alkyl optionally substituted with hydroxy, halogen, cyano, alkoxy, aryloxy, dialkylamino, arylalkylamino or diarylamino; or aralkyl;

$R^1$ may be covalently linked to A, $R^5$, $R^6$ and/or $R^7$, in which case —$R^1$—A— or —$R^1$—$R^5$— represents low alkylene, unsubstituted or substituted with alkyl, hydroxy, alkoxycarbonyl, alkoxy or dialkylamino, —R$^1$—R$^6$— represents ethylene or propylene, unsubstituted or substituted with alkyl, hydroxy, alkoxy or dialkylamino, and/or —R$^1$—R$^7$— represents methylene, propylene or butylene unsubstituted or substituted with alkyl, hydroxy, alkoxycarbonyl, alkoxy or dialkylamino;

R$^2$ is alkyl optionally substituted with aryl, heteroaryl, alkoxy, aryloxy, cyano, dialkylamino, arylalkylamino, diarylamino or halogen;

aryl optionally substituted with alkyl, aryl, heteroaryl, halogen, alkoxy, aryloxy, dialkylamino, alkylarylamino, diarylamino, halogen, cyano, alkoxycarbonyl or aminocarbonyl;

heteroaryl optionally substituted with alkyl, aryl, heteroaryl, halogen, alkoxy, aryloxy, dialkylamino, alkylarylamino, diarylamino, halogen, cyano, alkoxycarbonyl or aminocarbonyl; and R$^3$ is cyano, nitro, —CO—R' or —C(OH)—R', R' being alkyl, alkyl substituted with halogen, aryl, aryl substituted with alkyl, aryl, heteroaryl, halogen, alkoxy, aryloxy, dialkylamino, alkylarylamino, diarylamino, halogen, cyano, alkoxycarbonyl or aminocarbonyl or heteroaryl; or —SO$_2$R", R" being alkyl or substituted or unsubstituted aryl, R$^4$ is hydrogen or COZ, Z being substituted or unsubstituted alkyl, aryl, arylamino or alkylamino; and pharmaceutically acceptable salts thereof;

the method comprising the steps of:

(a) attachment of a compound having a free or protected primary or secondary amino group of the formula A—NH—R$^1$ to a substrate (S) via a chemical bond or linker (L), optionally followed by a deprotection step, for generating a substrate-bound free primary or secondary amine of the formula S—L—A'—N(R$^1$)H, wherein R$^1$ is as defined above, A' is a chemical bond or a group of formula

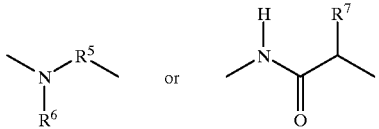

wherein

R$^5$, R$^6$ and R$^7$ are as defined above;

R$^5$ and R$^6$ may be covalently linked to each other by a covalent bond or an additional alkylene group R$^5$, thereby giving rise to a fragment of the type shown below

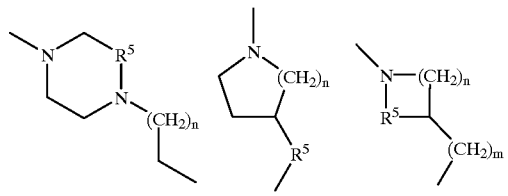

-continued

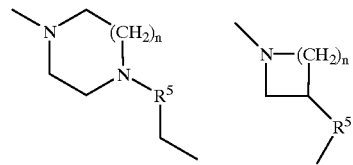

wherein n and m are as defined above;

(b) acylation of the substrate-bound free primary or secondary amine of the formula S—L—A'—N(R$^1$)H with a cyanoacetic acid derivative of the structure NC—CH$_2$—COX, wherein X is a hydroxy group or a leaving group;

(c) reaction of the resulting substrate-bound amide of the formula S—L—A'—N(R$^1$)—CO—CH$_2$—CN wherein R$^1$ is as defined above, with an aliphatic or aromatic isothiocyanate of the structure R$^2$—NCS wherein R$^2$ is as defined above, in the presence of a base;

(d) alkylation of the resulting substrate-bound intermediate of the formula S—L—A'—N(R$^1$)—CO—C(CN)=C(NHR$^2$)—SH with an alkylating agent of the structure R$^3$—CH$_2$—X, wherein R$^3$ is as defined above and X is a leaving group for nucleophilic displacement, under neutral or acidic conditions, followed by treatment with a base, in order to prepare a compound of formula II

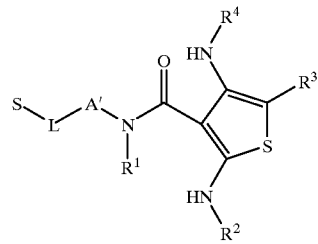

wherein S, L, A', R$^1$, R$^3$ and R$^4$ are as defined above; and

R$^2$ is alkyl optionally substituted with aryl, heteroaryl, alkoxy, aryloxy, cyano, hydroxy, dialkylamino, arylalkylamino, diarylamino or halogen;

aryl optionally substituted with alkyl, aryl, heteroaryl, halogen, alkoxy, aryloxy, dialkylamino, alkylarylamino, diarylamino, halogen, cyano, alkoxycarbonyl or aminocarbonyl; heteroaryl optionally Substituted with alkyl, aryl, heteroaryl, halogen, alkoxy, aryloxy, dialkylamino, alkylarylamino, diarylamino, halogen, cyano, alkoxycarbonyl or aminocarbonyl; and pharmaceutically acceptable salts thereof; and (e) subjection of the resulting substrate-bound compound of formula II to cleavage conditions in order to prepare the compound of formula I.

2. The method according to claim 1, further comprising the step of screening the final product of formula I directly against a specific receptor or enzyme.

3. The method according to claim 1, wherein said compound having a free or protected primary or secondary amino group is first coupled to the linker whereafter the linker is attached to the substrate.

4. The method according to claim 1, wherein the substrate is first attached to the linker whereafter said compound having a free or protected primary or secondary amino group is coupled to the linker.

5. The method according to claim 1, wherein the base for the reaction of the isothiocyanate with the cyanoacetamide and for the cyclization to the thiophene is 1,8-diazabicyclo[5.4.0]undec-7-ene (DBU).

6. The method according to claim 1, wherein the cyanoacetic acid derivative is the symmetrical anhydride.

* * * * *